(12) United States Patent
Hashmi et al.

(10) Patent No.: US 10,849,666 B2
(45) Date of Patent: Dec. 1, 2020

(54) PHALANGEAL HEAD PLATE

(71) Applicant: DePuy Synthes Products, Inc., Raynham, MA (US)

(72) Inventors: Adam Hashmi, West Chester, PA (US); Mirko Rocci, Zuchwil (CH); Lynn Kelly, West Chester, PA (US); Fabienne Fischer, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 182 days.

(21) Appl. No.: 16/213,330

(22) Filed: Dec. 7, 2018

(65) Prior Publication Data
US 2019/0105089 A1 Apr. 11, 2019

Related U.S. Application Data

(63) Continuation of application No. 14/320,436, filed on Jun. 30, 2014, now Pat. No. 10,182,855.

(51) Int. Cl.
*A61B 17/88* (2006.01)
*A61B 17/80* (2006.01)

(52) U.S. Cl.
CPC ...... *A61B 17/8061* (2013.01); *A61B 17/8057* (2013.01); *A61B 17/8085* (2013.01)

(58) Field of Classification Search
CPC combination set(s) only.
See application file for complete search history.

(56) References Cited

U.S. PATENT DOCUMENTS

| | | | |
|---|---|---|---|
| 4,776,330 A | 10/1988 | Chapman et al. | |
| 8,118,846 B2* | 2/2012 | Leither | A61B 17/8057 606/280 |
| 8,162,996 B2 | 4/2012 | Schelling | |
| 8,167,918 B2 | 5/2012 | Strnad et al. | |
| 8,172,884 B2 | 5/2012 | Bouman | |
| 8,292,898 B2 | 10/2012 | Castaneda et al. | |
| 2011/0264149 A1 | 10/2011 | Pappalardo et al. | |
| 2012/0078252 A1 | 3/2012 | Huebner et al. | |
| 2015/0366597 A1 | 12/2015 | Kobayashi et al. | |

FOREIGN PATENT DOCUMENTS

| | | |
|---|---|---|
| CN | 101091670 | 12/2007 |
| CN | 102164554 | 8/2011 |
| CN | 203576615 | 5/2014 |
| EP | 2623059 | 8/2013 |

(Continued)

*Primary Examiner* — Sameh R Boles
(74) *Attorney, Agent, or Firm* — Fay Kaplun & Marcin, LLP (57) ABSTRACT

A bone plate sized and shaped for fixation to a phalangeal bone includes a head extending from a first end to a second end and having first, second and third fixation element holes extending therethrough and arranged in a triangular configuration on the head, an outer wall of the head having a triangular shape corresponding to the triangular configuration, a bone contacting surface of the head being contoured to conform to the anatomy of a lateral surface of a phalangeal head and a shaft extending from the head, the shaft including fourth and fifth plate holes separated from one another by an elongated fixation element hole elongated in a direction parallel to a longitudinal axis of the shaft.

11 Claims, 5 Drawing Sheets

(56) References Cited

FOREIGN PATENT DOCUMENTS

| | | |
|---|---|---|
| JP | S53-132191 | 11/1978 |
| JP | 2006-506194 | 2/2006 |
| JP | 2006-280951 | 10/2006 |
| JP | 2007-190209 | 8/2007 |
| JP | 2008-6285 | 1/2008 |
| JP | 2011-502574 | 1/2011 |
| JP | 2011-510799 | 4/2011 |
| JP | 2011-245306 | 12/2011 |
| JP | 2013-525026 | 6/2013 |
| WO | 2013/036362 | 3/2013 |
| WO | 2015/195399 | 12/2015 |

* cited by examiner

PHALANGEAL HEAD PLATE

PRIORITY CLAIM

The present application is a Continuation of U.S. patent application Ser. No. 14/320,436 filed on Jun. 30, 2014. The entire disclosures of the above application(s)/patent(s) are incorporated herein by reference.

FIELD OF THE INVENTION

The present invention generally relates to bone plates for the fixation of fractures of the hand and methods of coupling these plates to bone.

BACKGROUND

Current systems and methods for the fixation of fractures are limited in the placement and orientation of plates over the bone. For example, many of these plates are limited to a dorsal placement over a target bone preventing a surgeon from selecting a location optimized for the fracture.

SUMMARY OF THE INVENTION

The present invention is directed to a bone plate sized and shaped for fixation to a phalangeal bone, the bone plate comprising a head extending from a first end to a second end and having first, second and third fixation element holes extending therethrough and arranged in a triangular configuration on the head, an outer wall of the head having a triangular shape corresponding to the triangular configuration, a bone contacting surface of the head being contoured to conform to the anatomy of a lateral surface of a phalangeal head. The bone plate further comprises a shaft extending from the head, the shaft including fourth and fifth plate holes separated from one another by an elongated fixation element hole elongated in a direction parallel to a longitudinal axis of the shaft.

BRIEF DESCRIPTION OF THE DRAWINGS

Several embodiments of the invention will be described in the following by way of example and with reference to the accompanying drawings in which.

DETAILED DESCRIPTION

The exemplary embodiments may be further understood with reference to the following description and the appended drawings, wherein like elements are referred to with the same reference numerals. The exemplary embodiments relate to apparatus and methods for the treatment of fractures and, in particular, to devices for fixing fractures of the phalanges. More specifically, the exemplary bone fixation plates may be used for the fixation of uni- and bi-condylateral fractures of the middle and proximal phalangeal head. Exemplary embodiments describe a bone fixation plate having a head at a first end with an elongated shaft extending therefrom to a second end. The head of the exemplary bone plate is generally triangular with first, second and third side walls angled relative to one another to form a triangular outer profile. The head of this exemplary plate includes first, second and third variable angle fixation holes positioned adjacent corners of the triangle enclosed by the head. The shaft includes an elongated hole extending along a hole axis parallel to a longitudinal axis of the bone plate. As will be described in greater detail later on, the elongated hole aids in positioning the bone plate over a target portion of the bone. The shaft further comprises first and second variable angle locking holes on either side of the elongated hole, the first and second variable angle holes being offset from the longitudinal axis of the bone plate, as will also be described in greater detail later on. A plurality of notches is distributed over the outer border of the bone plate. A first notch located at the first end of the head between first and second variable angle holes is sized and shaped to receive a collateral ligament when the plate is positioned over a phalanx head of a metacarpal reducing interference from the plate with surrounding ligaments and tissues. A bone contacting surface of the head has a curvature selected to conform to a curvature of a lateral wall of proximal phalanx head to ensure flush seating of the plate thereover. As will be described in greater detail later on, the exemplary shape, size and contour of the exemplary bone plate permits the bone plate to be positioned along a lateral wall of metacarpal and further permits the bone plate to be positioned further dorsally on the metacarpal than currently available plates. It should be noted that the terms "proximal" and "distal" as used herein, refer to a direction toward (proximal) and away from (distal) a core of the body. For example, a direction from the hand to the elbow is proximal while a direction from the elbow to the hand is distal. Furthermore, when using these terms in reference to a plate to be attached to a bone, proximal will refer to a direction along the plate when it is attached to a target bone in a desired orientation.

As shown in FIGS. 1-10, an exemplary bone plate 100 has a head 104 at a first end 102 thereof and a shaft extending therefrom along a central longitudinal axis 110 to a second end 106. The head 104 is substantially triangular and includes first, second and third variable angle plate holes 112, 114, 116 extending therethrough from a bone contacting surface 118 to an upper surface 120. Trajectories for the plate hole axes 113, 115, 117 are selected to capture common fracture patterns while avoiding the articular surface of the bone and minimizing interference with adjacent collateral ligaments. For example, computed tomography scan data may be used to select trajectories for these hole axes 113, 115, 117 optimized to suit the most commonly encountered anatomy of the target portion of bone while the variable angle feature of the plate holes 112, 114, 116 permits a surgeon to vary the angle at which screws are inserted through these holes (relative to the hole axes) to optimize these trajectories to suit the anatomy of a particular patient.

Figure 1:
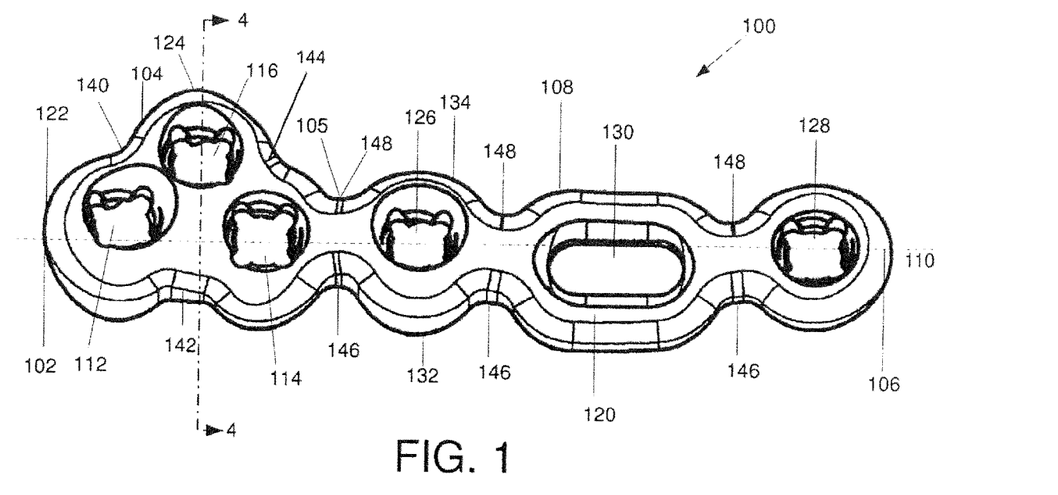
FIG. 1 shows a first perspective view of a bone fixation plate according to a first exemplary embodiment of the invention.
Figure 2:
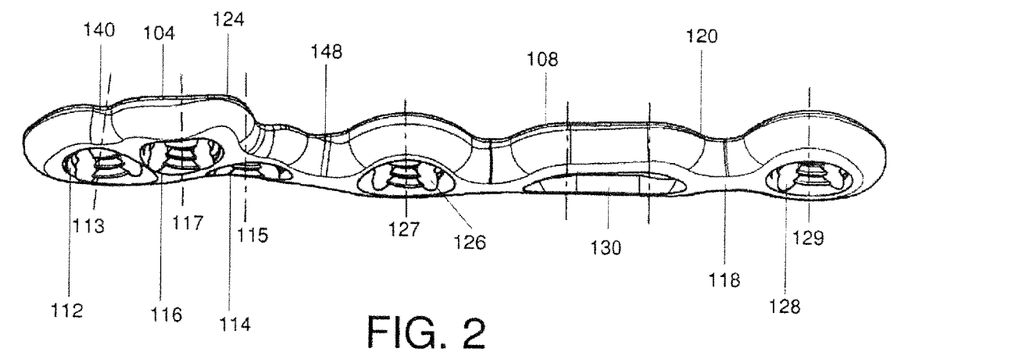
FIG. 2 shows a second perspective view of the bone fixation plate of FIG. 1.
Figure 3:
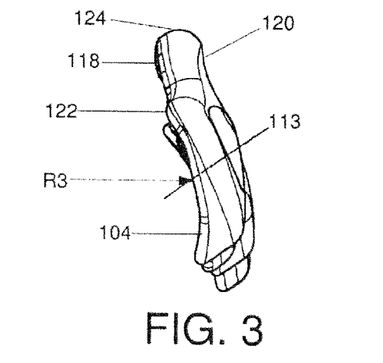
FIG. 3 shows a third perspective view of the bone fixation plate of FIG. 1.
Figure 6:
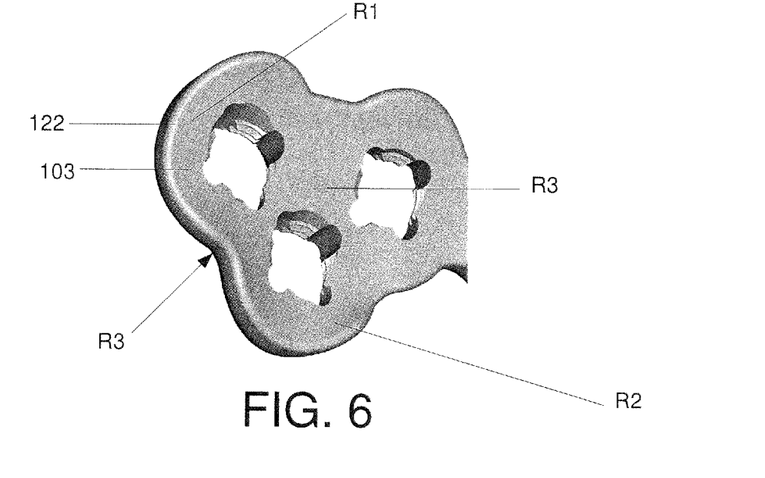
FIG. 6 shows a perspective view of a bone-contacting surface of a head of the bone fixation plate of FIG. 1.
Figure 7:
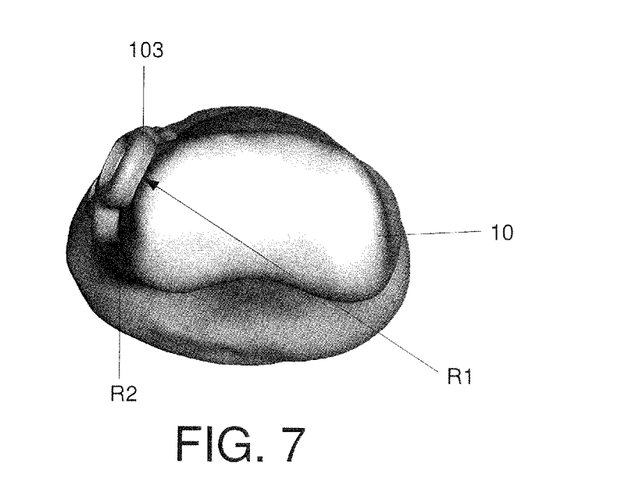
FIG. 7 depicts a first perspective view of the bone fixation plate of FIG. 1 over a bone.
Figure 8:
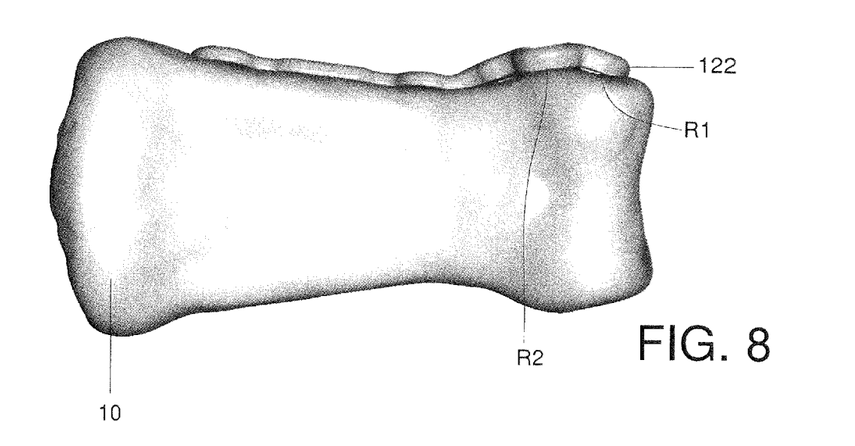
FIG. 8 depicts a second perspective view of the bone fixation plate of FIG. 1 over a bone.

The triangular configuration of the head 104 is selected to permit the bone plate 100 to be seated closer to a head of a target bone than possible with conventional plates. Specifically, a first corner 122 of the triangular head 104 is located at a proximalmost end 102 of the bone plate 100. Thus, the diameter of the head 104 is smallest at the proximalmost end 102, increasing to a maximum diameter at a second corner 124 of the triangular head. As those of skill in the art will understand, the reduced diameter at the first corner 122 permits the bone plate 100 to be seated closer to or on a head of the target bone than would be possible with a bone plate with a larger profile. As shown in FIGS. 3, 6 and 7, a predetermined portion 103 of the head 104 at the first corner 122 may be curved downward toward a palmar surface of the bone in an implanted configuration. Specifically, the portion 103 may be curved toward the bone 10 so that a bone-contacting surface thereof has a first curvature R1 with a radius of curvature of 3 mm. It is noted that this value is exemplary only and that other dimensions are envisioned within the scope of the invention. In another embodiment, the radius of curvature R1 may be 1-4 mm. This downward curvature aids in reduction of the fracture.

As shown in FIGS. 6 and 7, a predetermined portion 107 of the head 104 at the second corner 124 may also be curved downward toward the bone in a direction toward a palmar surface of the bone in an implanted configuration. Specifically, the portion 107 may be curved toward the bone 10 so that a bone-contacting surface thereof has a second curvature R2 with a radius of curvature of 5 mm. It is noted that this value is exemplary only and that other dimensions are envisioned within the scope of the invention. In another embodiment, the radius of curvature R2 may be 3-6 mm. This downward curvature aids in reduction of the fracture.

Figure 4:
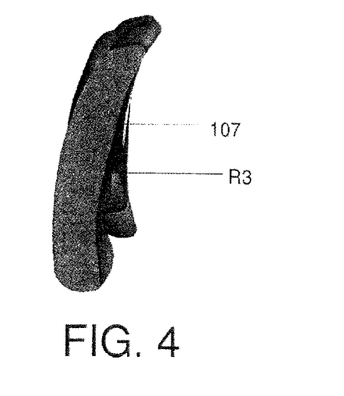
FIG. 4 shows a cross-section of the bone fixation plate of FIG. 1 taken along the line 4-4 and depicted without the plate hole intersecting the line 4-4 for clarity.
Figure 5:
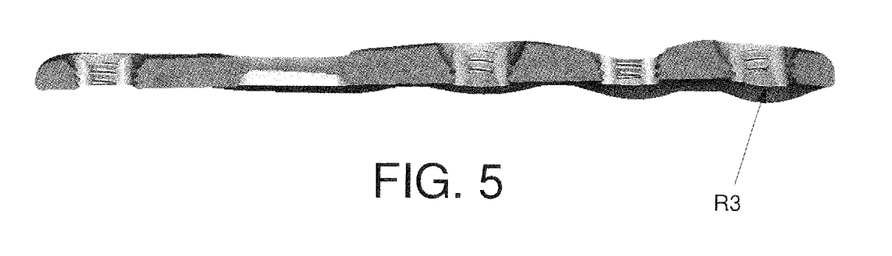
FIG. 5 shows a cross-section of the bone fixation plate of FIG. 1 taken along a central longitudinal axis thereof.

A curvature of the bone-contacting surface 118 is selected to conform to the curvature of the lateral aspect of the proximal phalangeal head and to ensure a flush fit therewith. In one embodiment, the bone-contacting surface 118 of the head 104 includes curvatures of varying radii. As shown in FIGS. 3-10, the bone-contacting surface 118 includes a plurality of curvatures of varying radii along a length thereof, the curvatures being selected to conform to the curvature of a bone 10. Specifically, a bone-contacting surface 118 of the head 104 includes a third curvature R3 having a radius of curvature of 6-12 mm. It is noted that this value is exemplary only and that other dimensions are envisioned within the scope of the invention. The radius of curvature R3 is centered about the first plate hole 112 and extends parallel to the central longitudinal axis 110. In another embodiment, the third curvature R3 may be offset relative to the central longitudinal axis 110. FIG. 4 depicts a cross-section of the bone plate 100 taken along the line 2-2 and depicted without the second plate hole 114 for clarity. As shown in FIG. 4, the third curvature R3 is defined by an arc of a cylinder positioned against the bone plate 100 and extending along an axis parallel or offset with respect to the axis 116.

The head 104 includes a first notch 140 at the proximal end 102 between the first and second plate holes 112, 114. The notch 140 has a substantially rounded shape and is offset from the longitudinal axis 110. In an exemplary embodiment, a shape of the notch 140 corresponds to an arc of a circle. In one embodiment, the notch 140 has a third radius of curvature of 0.7 mm. However, this radius of curvature is exemplary only and other values may be used without deviating from the scope of the invention. The notch 140 is positioned to receive a guide-wire (not shown) inserted in a condyle of a target bone, as will be described in greater detail with respect to the exemplary method below. Furthermore, the notch 140 is sized to accommodate the collateral ligament therein when positioned in a target orientation over the bone. In another embodiment, the notch 140 may have a non-circular shape (e.g., oblong, etc.) without deviating from the scope of the invention.

Figure 10:
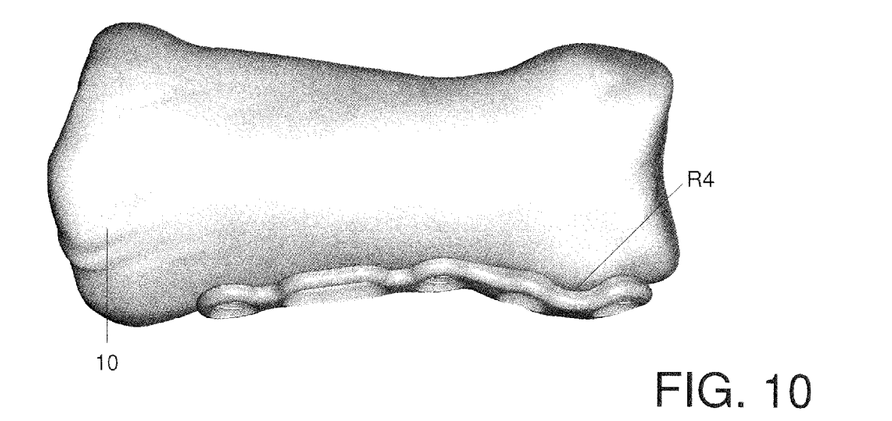
FIG. 10 depicts a fourth perspective view of the bone fixation plate of FIG. 1 over a bone.

The head 104 further comprises a second notch 142 between the first and third plate holes 112, 116. The notch 142 is formed as a cutout extending into the first lateral wall 132 and having an oblong shape. A third notch 144 extends into the head 104 along a second lateral wall 134 of the bone plate 100. The first, second and third notches 140, 142, 144 reduce an outer profile of the bone plate 100 without compromising the structural integrity thereof. The bone-contacting surface of the head 104 at the second notch 142 is curved with a fourth curvature R4 having a radius of curvature of 3-6 mm, as shown in FIG. 10.

A reduced diameter neck 105 separates the head 104 from the shaft 108. The shaft 108 extends distally from the neck 105 to the distal end 106 and includes fourth and fifth variable angle plate holes 126, 128. In one embodiment, a trajectory 127 of the fourth plate hole 126 is oriented to extend toward a first lateral wall 132 of the bone plate 100 from the upper surface 120 to the bone contacting surface 118. A trajectory 129 of the fifth plate hole 128 may be different than the trajectory 127. In a preferred embodiment, trajectories 113, 115, 117 are angled toward a center of the target bone and trajectories 113, 115, 117 are angled to diverge from one another. It is noted, however, that these trajectories are exemplary only and any other orientation of the trajectories 113, 115, 117, 127, 129 may be employed in an alternate embodiment. The trajectories 127, 129 may assume any path selected to lockingly engage the bone without extending through an opposing cortical surface thereof. The shaft 108 also includes an elongated hole 130 elongated in a direction extending parallel to the longitudinal axis 110. An axial length (of the elongated hole 130 is at least larger than a diameter of the first through fifth plate holes 112, 114, 116, 126, 128 while a width of the elongated hole 130 may be equivalent to the diameter of the first through fifth plate holes 112, 114, 116, 126, 128. In a preferred embodiment, the first through fifth plate holes 112, 114, 116, 126, 128 are 1.5 mm variable angle holes. However, in another embodiment, one or more of the first through fifth plate holes 112, 114, 116, 126, 128 may be formed as standard locking holes having a diameter of 1.3 mm. Still further, it is noted that any other diameter of the holes may be used without deviating from the scope of the invention to conform to the requirements of a particular procedure. As will be described in greater detail below with respect to the exemplary method, the elongated hole 130 permits a surgeon or other user to slide the bone plate 100 over the bone within a predetermined range (i.e., corresponding to a length of the elongated hole 130) prior to locking the bone plate 100 in place. In one embodiment, the elongated hole 130 allows for 3 mm. of movement along the longitudinal axis 110 while also permitting rotation of the bone plate 100 therearound, as will also be described in greater detail later. The exemplary elongated plate hole 130 extends orthogonally through the bone plate from the upper surface 120 to the bone contacting surface 118. The elongated hole 130 bypasses the need for a guidewire to position the bone plate 100 over the bone. Rather, since the bone plate 100 is adjustable relative to a bone screw inserted through the elongated hole 130, a surgeon or other user may use the elongated hole 130 itself as a guide when positioning the bone plate 100 over the bone.

The fourth and fifth holes 126, 128 are axially aligned along the shaft 108 while the elongated hole 130 is offset relative to the longitudinal axis 110 toward the first lateral wall 132. The offset position of the elongated hole 130 increases the stability of the connection between the bone plate 100 and the target bone. The bone-contacting surface 118 of the shaft 108 is curved along the longitudinal axis 110 to conform to the substantially cylindrical shape of the target portion of the bone over which the shaft 108 will be seated. In one embodiment, the length of the shaft 108 may include a single uniform curvature. In another embodiment, the bone contacting surface 118 of the shaft 108 may include a plurality of curves selected to ensure that the shaft 108 is seated flush over the bone.

The shaft 108 also includes a plurality of first webbed portions 146 extending along the first lateral wall 132 between each of the holes 116, 126, 130, 128 and a plurality of second webbed portions 148 extending along the second lateral wall 134 between each of the holes 116, 126, 130, 128. The first and second webbed portions 146, 148 are formed as notches extending into the width of the bone plate 100 reducing a profile thereof while maintaining the structural integrity of the bone plate 100. The first and second webbed portions 146, 148 as well as the notches 140, 142, 144 are sized to maintain a minimum desired clearance remains around the boundary of each of the plate holes of the bone plate 100. An outer periphery of the bone plate 100 may include a rounded taper to further reduce the profile as would be understood by those skilled in the art.

Figure 9:
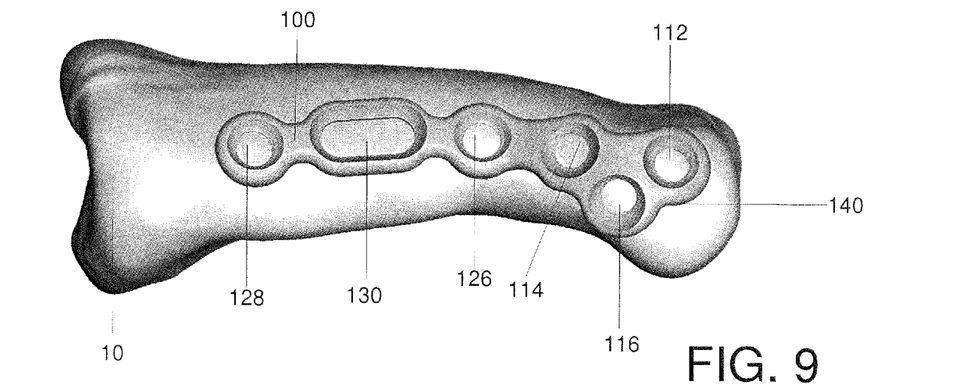
FIG. 9 depicts a third perspective view of the bone fixation plate of FIG. 1 over a bone.

In accordance with an exemplary method according to the invention, the bone plate 100 is positioned over a target portion of a bone 10. Specifically, the bone plate 100 is positioned over a lateral or medial side of the bone adjacent the phalangeal head, as shown in FIG. 9. The surgeon or other user approximates the desired position of the bone plate 100 over the bone 10. A cortex screw (not shown) is then inserted through the elongated hole 130 and into the bone 10 to a first depth sufficient to hold the bone plate 100 over the bone 10 while still permitting movement of the bone plate 100 relative to the bone 10. The bone plate 100 is then slid axially along the length of the elongated hole 130 and/or rotated about the cortex screw (not shown) until a final target position has been achieved. The exemplary system and method according to the invention bypasses the need for pre-drilling holes in the bone. Rather, once the target position has been achieved, bore holes are drilled through any of the first, second, third, fourth and fifth plate holes 112, 114, 116, 126, 128 and into the bone 10. In contrast, present bone fixation systems require the insertion of a guidewire into the bone prior to the placement of the bone plate over the bone, thus requiring that a final position of the bone plate 100 be selected prior to the placement of the bone plate over the bone. This method may lead to reduced accuracy in placement, especially in the fixation of phalangeal bones where even the smallest deviation, (e.g., in millimeters) from a correct position may lead to less than optimum fixation. The exemplary bone plate 100, on the other hand, permits adjustment of the position of the bone plate 100 even after the bone plate 100 has been initially secured to the bone, thereby ensuring that the final position of the bone plate 100 captures all fragments of the bone 10 while avoiding interference with ligaments, tendons or other tissue.

Once the bone plate 100 has been moved to the target position, a guidewire (not shown) is inserted in the center of a condyle of the bone 10 within the first notch 140. The guidewire 140 serves to retain the bone plate 100 in the target configuration while bone screws are inserted into plate holes thereof. In another embodiment, this optional step may be omitted. A bone screw (not shown) is then inserted into the first plate hole 112, followed by a bone screw (not shown) in the second plate hole 114. Bone screws (not shown) may then be inserted into any of the third, fourth and fifth plate holes 116, 126, 128 depending on the fracture pattern. The bone screw inserted into the elongated plate hole 130 may be tightened to firmly engage the bone plate 100.

Figure 11:
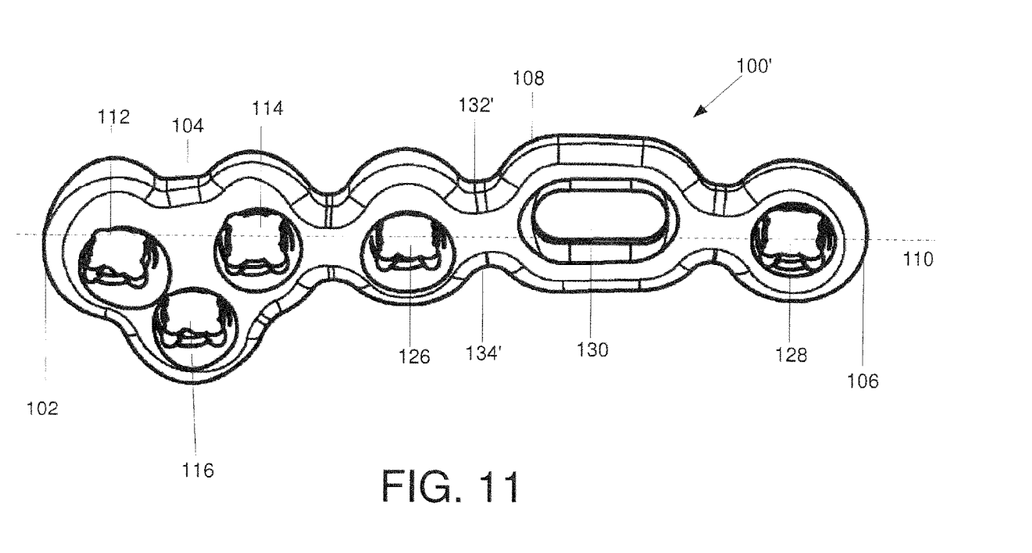
FIG. 11 shows a bone plate according to another embodiment of the invention.

The exemplary bone plate 100 depicted in FIGS. 1-10 is configured for placement in right hand bones. For fixation of bones of the left hand, a bone plate 100' may be used, as shown in FIG. 11. The bone plate 100' is formed substantially similarly to the bone plate 100, with like elements referenced with like reference numerals, except as noted below. First and second lateral walls 132', 134' are reversed in the bone plate 100', resulting in a mirror-image of the bone plate 100.

Figure 12:
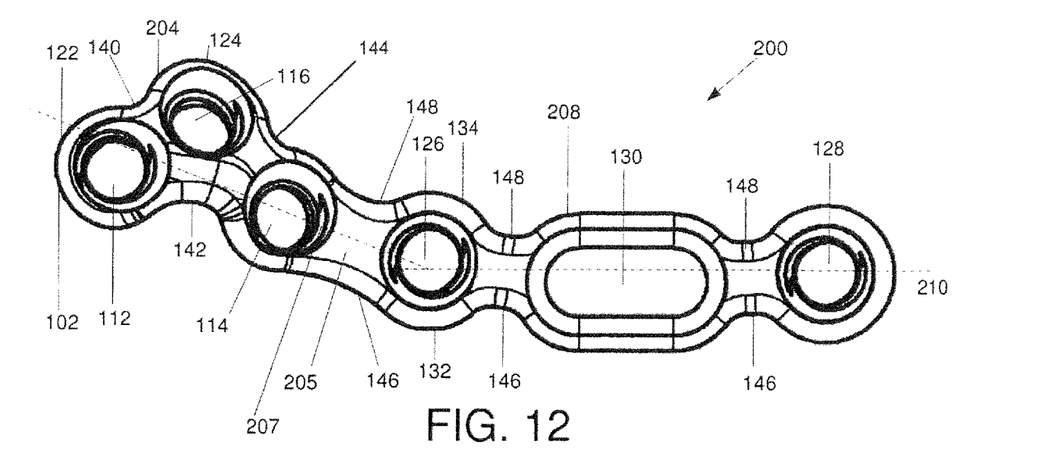
FIG. 12 shows a first perspective view of a bone plate according to yet another embodiment of the invention.
Figure 13:
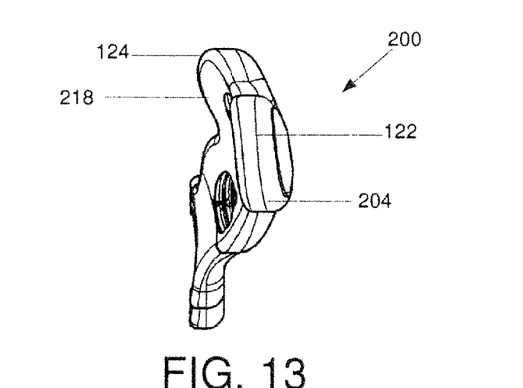
FIG. 13 shows a second perspective view of the bone plate of FIG. 12.
Figure 14:
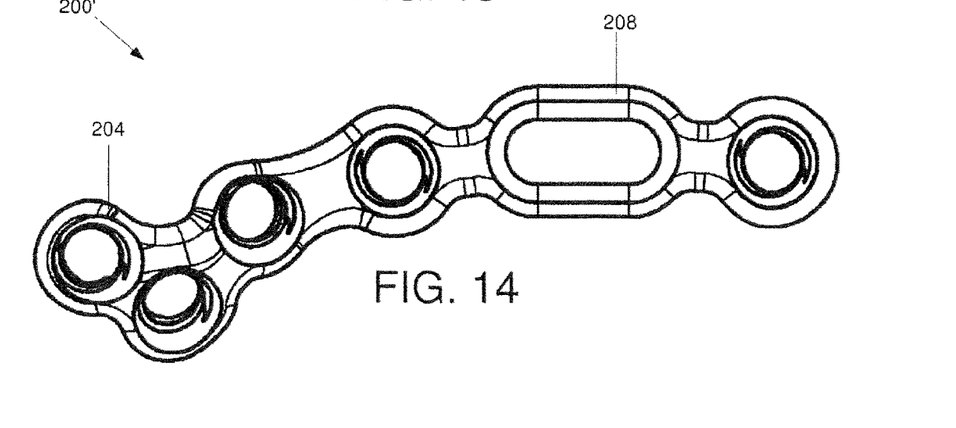
FIG. 14 shows a bone plate according to another embodiment of the invention.

FIGS. 12-14 depict a bone plate 200 according to another embodiment of the invention. The bone plate 200 is formed substantially similar to the bone plate 100, wherein like elements have been referenced with like reference numerals, except as noted below. However, whereas the head 104 and shaft 108 of bone plate 100 are substantially aligned along the longitudinal axis 110, the bone plate 200 is configured so that a head 204 thereof is angled relative to a shaft 208 thereof specifically, a neck region 205 extending between the head 204 and shaft the 208 extends along a longitudinal axis 207 angled relative to a longitudinal axis 210 of the shaft 208. The angle of the longitudinal axis 207 relative to the longitudinal axis 210 is selected so that no portion of the head 204 intersects the longitudinal axis 210. It is noted, however, that any other angle may be selected without deviating from the scope of the invention. The exemplary bone plate 200 is selected to span multiple surfaces of a target bone, thereby increasing the strength of the connection between the bone plate 200 and the fragments of the target bone. For example, the head 204 may be seated on a lateral surface of the bone while the shaft 208 extends from the lateral surface to a dorsal surface of the bone. A curvature of a bone-contacting surface 218 of the bone plate 200 is selected to conform to the desired placement of the bone plate 200. The bone plate 200 is selected for placement in bones of the right hand. FIG. 14 depicts a bone plate 200' formed for insertion on bones of the left hand. As with the bone plates 100, 100', the bone plate 200' is a mirror-image of the bone plate 200.

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A method for bone fixation, comprising:

positioning a bone plate over a lateral surface of a phalangeal bone so a head of the bone plate is seated over a phalangeal head, the bone plate including a head extending from a first end to a second end and having first, second and third fixation element holes extending therethrough arranged in a triangular configuration on the head, an outer wall of the head having a substantially triangular shape corresponding to the triangular configuration of the first, second and third fixation element holes, a bone contacting surface of the head being contoured to conform to the anatomy of a lateral surface of the phalangeal head, the bone plate including a shaft extending from the head;

inserting a first fixation element into an elongated fixation element hole extending through the shaft, wherein the elongated fixation element hole is elongated in a direction parallel to a longitudinal axis of the shaft; and sliding the bone plate over the phalangeal bone within a range of motion limited by a length of the elongated fixation element hole to a desired location over the lateral surface of the phalangeal bone.

2. The method of claim 1, further comprising:

inserting, after sliding the bone plate to the desired location, a second fixation element into the first fixation element hole.

3. The method of claim 2, further comprising:

inserting a third fixation element into the second fixation element hole to lock the bone plate over the phalanx.

4. The method of claim 1, further comprising:

inserting a guidewire into a target location in the phalangeal head so that, when the bone plate is positioned with the guidewire received in a notch on the first end between the first and second fixation element holes, the guidewire maintains a desired position of the bone plate over the phalangeal bone prior to insertion of second and third fixation elements into the bone.

5. The method of claim 4, further comprising:

after the bone plate has been positioned in a desired position over the phalangeal bone, drilling a hole into the bone via one of the first, second, and third fixation element holes.

6. The method of claim 4, wherein the notch is formed as an indentation on an outer wall of the bone plate between the first and second fixation element holes.

7. The method of claim 1, further comprising:

rotating the bone plate about the first fixation element to the desired location prior to insertion of second and third fixation elements thereinto.

8. The method of claim 1, wherein a first corner at the first end of the triangular head located adjacent to the first fixation element hole has a diameter reduced compared to a diameter of a second corner located adjacent to the second fixation element hole, the triangular head defining a third corner adjacent to a neck connecting the head to the shaft.

9. The method of claim 8, wherein the head is generally concave to correspond to an anatomy of the phalangeal head.

10. The method of claim 1, further comprising:

inserting a fourth fixation element into one of fourth and fifth fixation element holes located on the shaft and separated from one another by the elongated fixation element hole.

11. The method of claim 10, wherein trajectories of the fourth and fifth fixation element holes extend along hole axes converging toward a center of the bone.

* * * * *